(12) United States Patent
Hartwig et al.

(10) Patent No.: US 10,444,110 B2
(45) Date of Patent: Oct. 15, 2019

(54) SYSTEM AND METHOD FOR INSPECTING PARTS USING FREQUENCY RESPONSE FUNCTION

(71) Applicant: HONEYWELL FEDERAL MANUFACTURING & TECHNOLOGIES, LLC, Kansas City, MO (US)

(72) Inventors: Troy Hartwig, Kansas City, MO (US); Ben Brown, Kansas City, MO (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 498 days.

(21) Appl. No.: 14/941,258

(22) Filed: Nov. 13, 2015

(65) Prior Publication Data

US 2017/0138906 A1 May 18, 2017

(51) Int. Cl.
*G01M 7/02* (2006.01)
*G01N 29/04* (2006.01)
(Continued)

(52) U.S. Cl.
CPC ............ *G01M 7/022* (2013.01); *G01M 7/025* (2013.01); *G01N 29/043* (2013.01);
(Continued)

(58) Field of Classification Search
CPC .... G01N 29/04; G01N 29/046; G01N 29/069; G01N 29/07; G01N 29/09; G01N 29/11;
(Continued)

(56) References Cited

U.S. PATENT DOCUMENTS 5,214,960 A 1/1993 Tsuboi
5,425,272 A 6/1995 Rhodes
(Continued)

FOREIGN PATENT DOCUMENTS

WO WO9428388 12/1994
WO WO2006042520 4/2006

OTHER PUBLICATIONS

Standard Guide for Resonant Ultrasound Spectroscopy for Defect Detection in Both Metallic and Non-metallic Parts; ASTM International, 100 Barr Harbor Drive, PO Box C700, West Conshohocken, PA 19428-2959. United States; Designation: E2001-13.
(Continued)

*Primary Examiner* — Helen C Kwok
(74) *Attorney, Agent, or Firm* — Hovey Williams LLP

(57) ABSTRACT

A system and method for the non-destructive testing of additively manufactured parts. An input mechanism excites with an excitation force (e.g., a vibration) an additive manufacturing build platform on which the part is located to induce a dynamic response in the part. An output mechanism (e.g., a non-contact transducer) senses the induced dynamic response in the part. A processor determines and examines the relationship between the response and excitation to identify an indication of a defect in the part, and communicates an alert if the indication is identified. The processor may compare the phase, magnitude, coherence, or time delay of the relationship to a reference relationship and/or may compare the modal frequency or the modal damping to a reference to identify a deviation greater than a pre-established threshold.

23 Claims, 2 Drawing Sheets

Figure 1:
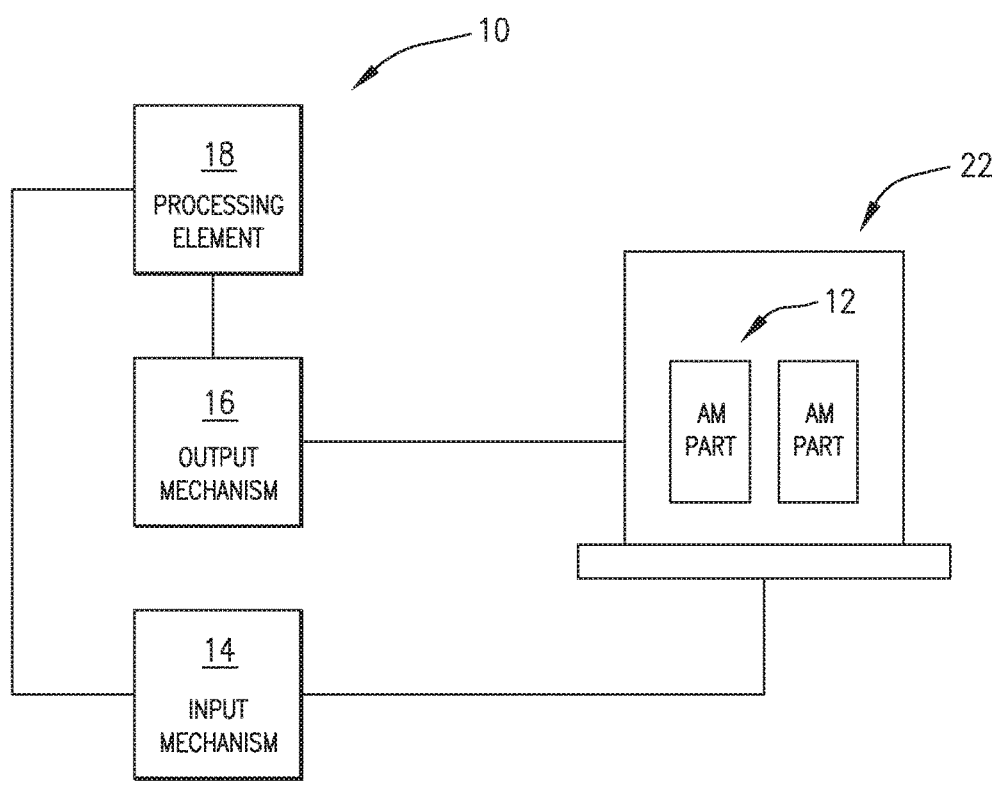

(51) Int. Cl.
G01N 29/11 (2006.01)
G01N 29/12 (2006.01)
G01N 29/44 (2006.01)

(52) U.S. Cl.
CPC ........... *G01N 29/045* (2013.01); *G01N 29/11* (2013.01); *G01N 29/12* (2013.01); *G01N 29/4427* (2013.01); *G01N 2291/012* (2013.01); *G01N 2291/014* (2013.01); *G01N 2291/015* (2013.01); *G01N 2291/2698* (2013.01)

(58) Field of Classification Search
CPC ...... G01N 29/14; G01N 29/22; G01N 29/222; G01N 29/221; G01N 29/228; G01N 29/2418; G01N 29/2431; G01N 29/2475; G01N 29/346; G01N 29/348; G01N 29/36
See application file for complete search history.

(56) References Cited

U.S. PATENT DOCUMENTS

| | | | | |
|---|---|---|---|---|
| 5,520,052 | A | 5/1996 | Pechersky | |
| 5,824,908 | A | 10/1998 | Schindel | |
| 6,065,342 | A * | 5/2000 | Kerr | G01N 29/14 367/127 |
| 6,519,500 | B1 * | 2/2003 | White | G05B 19/00 156/73.1 |
| 6,553,275 | B1 * | 4/2003 | Mazumder | G01L 5/0047 700/118 |
| 6,580,959 | B1 * | 6/2003 | Mazumder | G05B 19/4185 700/112 |
| 6,880,379 | B2 * | 4/2005 | Hedberg | G01N 3/30 702/38 |
| 6,925,346 | B1 * | 8/2005 | Mazumder | B23K 26/032 700/119 |
| 8,494,790 | B2 * | 7/2013 | Zhu | G01H 1/00 702/56 |
| 8,501,075 | B2 * | 8/2013 | Philippi | G01N 29/12 264/401 |
| 9,643,357 | B2 * | 5/2017 | Farah | B29C 67/0051 |
| 9,977,425 | B1 * | 5/2018 | McCann | G05B 23/0221 |
| 2006/0027021 | A1 * | 2/2006 | Choi | G01H 17/00 73/579 |
| 2008/0294354 | A1 * | 11/2008 | Zhu | G01H 1/00 702/39 |
| 2014/0216158 | A1 | 8/2014 | Sanabria | |
| 2015/0024233 | A1 * | 1/2015 | Gunther | G05B 19/41875 428/601 |
| 2015/0064047 | A1 * | 3/2015 | Hyde | B22F 3/1055 419/26 |
| 2015/0165683 | A1 * | 6/2015 | Cheverton | B29C 67/0088 382/141 |
| 2015/0273767 | A1 * | 10/2015 | Batchelder | G03G 15/224 264/401 |
| 2015/0314373 | A1 * | 11/2015 | Mironets | B22F 3/1055 419/30 |
| 2016/0059308 | A1 * | 3/2016 | Volk | B29C 67/0085 428/615 |
| 2016/0185048 | A1 * | 6/2016 | Dave | B33Y 50/02 700/119 |
| 2016/0375676 | A1 * | 12/2016 | Ritchie | B29C 67/0051 428/29 |
| 2017/0038342 | A1 * | 2/2017 | Clavette | B29C 67/0077 |
| 2017/0072466 | A1 * | 3/2017 | Zehavi | B22F 3/1055 |
| 2017/0072467 | A1 * | 3/2017 | Zehavi | B22F 3/1055 |
| 2017/0090462 | A1 * | 3/2017 | Dave | B33Y 50/00 |
| 2017/0097280 | A1 * | 4/2017 | Drescher | G01M 7/022 |
| 2017/0144250 | A1 * | 5/2017 | Gold | B23K 26/062 |
| 2017/0173692 | A1 * | 6/2017 | Myerberg | B22F 3/008 |
| 2017/0234837 | A1 * | 8/2017 | Hall | G01N 29/2431 73/602 |
| 2017/0284971 | A1 * | 10/2017 | Hall | G01N 29/04 |
| 2018/0001565 | A1 * | 1/2018 | Hocker | B33Y 40/00 |
| 2018/0200948 | A1 * | 7/2018 | Kuijpers | B29C 64/321 |

OTHER PUBLICATIONS

Standard Practice for Process Compensated Resonance Testing Via Swept Sine Input for Metallic and Non-Metallic Parts; ASTM International, 100 Barr Harbor Drive, PO Box C700, West Conshohocken, PA 19428-2959. United States; Designation: E2534-15.

* cited by examiner

SYSTEM AND METHOD FOR INSPECTING PARTS USING FREQUENCY RESPONSE FUNCTION

STATEMENT REGARDING FEDERALLY-SPONSORED RESEARCH OR DEVELOPMENT

This invention was made with Government support under Contract No.: DE-NA0002839 awarded by the United States Department of Energy/National Nuclear Security Administration. The Government has certain rights in the invention.

FIELD

The present invention relates to systems and methods for testing additively manufactured parts. More particularly, the present invention concerns a system and method for the non-destructive testing of additively manufactured parts.

BACKGROUND

Some parts are produced using additive manufacturing processes (e.g., three-dimensional printing) rather than traditional "subtractive" manufacturing process. Manufacturers employing additive processes desire effective and reliable testing methods to ensure quality control and to quantify the quality of parts. The quality and acceptability of additively manufactured parts may depend on various process parameters. For example, in selective laser melting (SLM) or electron beam melting (EBM), critical process parameters include powder characteristics and equipment setup parameters. In subtractive processes, material properties may be assessed based on samples of the bulk material from which the parts are fabricated. In additive processes, material properties may depend on the equipment setup parameters, such as scan speed and beam power. Therefore, the material properties of each additively manufactured part may be unique because density, microstructure, and mechanical properties are dependent on both powder characteristics and process parameters. Powder can be inspected and process parameters can be specified, but determining their cumulative effect on a part's material properties requires destructive testing of the part to confirm those properties. There are currently no suitable non-destructive tests to confirm the material properties of individual additively manufactured parts.

Resonant inspection techniques have been used to inspect parts produced by machining, casting, forging, and powered metallurgy processes. The parts are excited through direct contact, such as from impact hammers or piezoelectric actuators, and the response is measured with a microphone or with a direct contact piezoelectric actuator. The acceptability of an individual part is determined by comparing the peaks in a frequency spectrum of the response to those in a reference spectrum, wherein deviations in absolute frequency, relative frequencies, or peak amplitudes may be considered evidence of a defect. These techniques rely on contact with the parts being tested, either through impact by a hammer or contact with a piezoelectric transducer for excitation and response measurements. Such direct contact with the parts can directly affect the parts' responses and undermine the test results. Furthermore, because prior art processes input energy directly into the parts, the processes must be adjusted for the size and shape of each part being tested, which can lower efficiency.

Prior art testing methods rely solely on the frequency and amplitude of the response (or relative frequency and amplitude). As a result, they may be insufficiently sensitive to highly damped modes or modes with low radiation efficiency, which may undermine their ability to discriminate between acceptable and unacceptable parts. Also, prior art techniques use ultrasonic transducers which inherently have very little displacement capability, and therefore have very little power at low frequency. Ultrasonic transducers are only able to excite high frequency modes in parts and are not able to excite or detect low frequency modes, even though low frequency modes are likely to be most affected by the types of defects typically found in additively manufactured parts. Additionally, exciting and/or measuring parts through contact with ultrasonic transducers, which generally require acoustic coupling, adds to system damping.

This background discussion is intended to provide information related to the present invention which is not necessarily prior art.

SUMMARY

Embodiments of the present invention solve the above-described and other problems and limitations by providing a system and method for the non-destructive testing of one or more additively manufactured parts. In a first embodiment of the present invention, a system for the non-destructive testing of one or more parts manufactured using an additive manufacturing process may broadly comprise an input mechanism, an output mechanism, and a processing element. The input mechanism may be configured to excite with an excitation force an additive manufacturing build platform on which the one or more parts are located to induce a dynamic response in the one or more parts. The output mechanism may be configured to sense the induced dynamic response in the one or more parts. The processing element may be configured to determine the relationship between the excitation force and the dynamic response, to identify an indication of a defect in the one or more parts, and to electronically communicate an alert if the indication of the defect is identified.

In a second embodiment of the present invention, a method for the non-destructive testing of one or more parts manufactured using an additive manufacturing process may broadly comprise the following steps. An additive manufacturing build platform on which the one or more parts are located may be excited by an excitation force to induce a dynamic response in the one or more parts. The induced dynamic response in the one or more parts may be sensed with an output mechanism. The relationships between the excitation force and the dynamic response may be determined with an electronic processing element to identify an indication of a defect in the one or more parts, and an alert may be electronically communicated if the indication of the defect is identified.

Various implementations of the foregoing embodiments may include any one or more of the following features. A plurality of parts located on the additive manufacturing build platform may be tested simultaneously. The defect in the one or more parts may be, for example, porosities, voids, unfused powders, dimensional variations in parts, non-homogeneity in powder, improper microstructure, or cracks. The excitation force may be, for example, impulsive vibrations, swept sinusoid vibrations, or random input vibrations. Exciting the additive manufacturing build platform may include inputting the excitation force directly to the build platform so as to introduce the excitation force indirectly to the one or more parts located on the build platform. External damping imparted to the one or more parts may be minimized, including minimizing one or more forms of friction that might otherwise dissipate energy. The determined relationships may include a frequency response function, a coherence function, an autocorrelation function, a cross-correlation function, an auto-power spectrum, or a cross-power spectrum. These relationships may be further processed to estimate modal parameters, such as modal frequencies and modal damping, or to estimate the internal structural damping of the part. Examination of the relationships for identification of defects may include comparing a phase, a relative magnitude spectrum, a coherence spectrum, or a time delay between the output and the input to a reference relationship, or by comparing modal frequencies and modal damping or internal damping to reference values. The indication of the defect may be identified as a deviation of the determined relationship or parameter from the reference by an amount that is greater than a pre-established threshold. The pre-established threshold may be created by intentionally manufacturing a defective part with a known defect using the additive manufacturing process, examining the sensed induced frequency response of the defective part to identify the indication of the known defect, and basing the pre-established threshold on the identified indication. Additionally or alternatively, the pre-established threshold may be created using modeling and simulation.

This summary is not intended to identify essential features of the present invention, and is not intended to be used to limit the scope of the claims. These and other aspects of the present invention are described below in greater detail.

DRAWINGS

Figure 2:
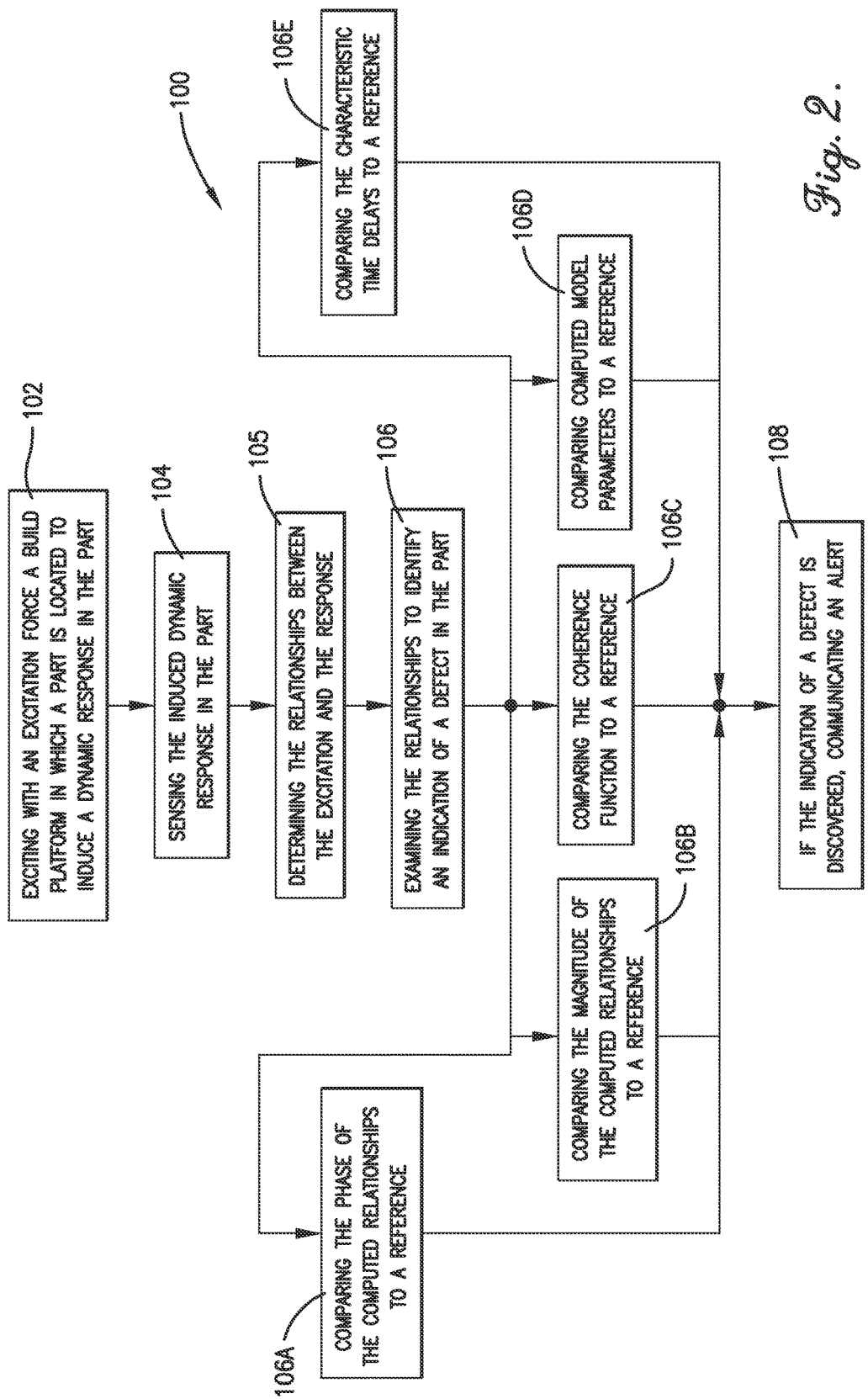

Embodiments of the present invention are described in detail below with reference to the attached drawing figures, wherein:

FIG. 1 is a block diagram of a system constructed in accordance with an embodiment of the present invention; and FIG. 2 is a flowchart of a method practiced in accordance with an embodiment of the present invention.

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment", "an embodiment", or "embodiments" mean that the feature or features referred to are included in at least one embodiment of the invention. Separate references to "one embodiment", "an embodiment", or "embodiments" in this description do not necessarily refer to the same embodiment and are not mutually exclusive unless so stated. Specifically, a feature, structure, act, etc. described in one embodiment may also be included in other embodiments, but is not necessarily included. Thus, particular implementations of the present invention can include a variety of combinations and/or integrations of the embodiments described herein.

Broadly characterized, the present invention provides a system and method for the non-destructive testing of additively manufactured parts by exciting an additive manufacturing build platform to induce a dynamic response in the parts located on the build platform, sensing the vibration-induced dynamic response, and examining a relationship between the dynamic response and the excitation force to detect a defect in the parts. In implementations, the testing may be performed in-situ or near in situ.

A part may be excited by introducing vibration excitation directly into the build platform, thereby avoiding direct contact with the part and avoiding introducing external damping or other influences on the part's response. Exciting the build platform may be accomplished using impulsive (e.g., by application of an impact hammer to the build platform), swept sinusoid, or random input vibrations applied to the additive manufacturing build platform so as to generate the dynamic response. Sensing the dynamic frequency response of the parts may be accomplished using non-contact motion transducers. Using non-contact motion transducers facilitates detecting modes that are highly damped and modes with low radiation efficiency, and again avoiding introducing external damping. Alternatively, the dynamic response may be measured with an acoustic or ultrasonic transducer, though this may result in less discriminatory ability.

The part's response to the vibration excitation may be determined by the part's geometry (e.g., shape, dimensions) and material properties (e.g., density, elasticity, internal damping). Defects in a part produced by an additive manufacturing process (such as SLM or EBM) may include porosity, voids, unfused powder, improper microstructure, and/or cracks. Such defects may effect the dynamic response of the vibrationally excited part, and such effects may include the frequency at which the part resonates, the amplitude of the response at resonance, the phase of the response relative to the excitation, the coherence function, and/or the time delay. In particular, the phase of the response may be sensitive to internal damping, and the types of defects occurring during additive manufacturing may be likely to affect the internal damping of the material.

The frequency response function (FRF) may be computed between the known input excitation force and the output dynamic response computed in the frequency domain. The frequency, amplitude, and phase of the part may be compared to a reference FRF measured in a part having known quality, or predicted from modelling and simulating acceptable parts. For example, peaks in the measured FRF for the newly created part may be compared to peaks in the reference FRF for a known acceptable part. Deviation of the measured FRF from the reference FRF by more than an allowable threshold may be interpreted as evidence of a defect and, potentially, an unacceptable part.

In one implementation, the structural integrity of the parts may be directly measured using a phase relationship between the input force and the measured response (i.e., the phase of the frequency response function). In particular, the additive manufacturing build platform may be vibrated and the amplitude and phase of the frequency response function may be determined and used to assess the structural integrity of the parts. Deviations of the actual response from the reference response which are greater than a pre-established allowable threshold may be used to identify defective parts. The allowable threshold may be pre-established by intentionally deviating additive manufacturing process parameters from ideal settings in order to produce reference part specimens with known unacceptable properties, and measuring their actual frequency response characteristics. Additionally, or alternatively, the allowable threshold may be pre-established using modelling and simulation of acceptable parts.

Referring to FIGS. 1 and 2, a system 10 and method 100 for the non-destructive testing of one or more parts 12 manufactured using an additive manufacturing process may broadly comprise an input mechanism 14, an output mechanism 16, and a processing element 18 configured to perform as follows. The input mechanism 14 may be configured to excite with an excitation force an additive manufacturing build platform 22 on which the part 12 is located to induce a dynamic response in the part 12, as shown in step 102. The excitation force may be, for example, impulsive vibrations, swept sinusoid vibrations, and random input vibrations. The input mechanism 14 may excite the build platform 22 by introducing the excitation force directly to the build platform 22 so as to introduce the excitation force indirectly to the part 12 located on the build platform 22.

The output mechanism 16 may be configured to sense the induced dynamic response in the part 12, as shown in step 104. The output mechanism 16 may directly or indirectly measure a mechanical or other response of the part 12. The output mechanism 16 may be a non-contact transducer. The processing element 18 may be configured to determine one or more relationships between the dynamic response output and the excitation force input, as shown in step 105. The processing element 18 may be configured to examine the relationship between the dynamic response output and the excitation force input to identify an indication of a defect in the part 12, as shown in step 106, and to communicate an alert if the indication of the defect is identified, as shown in step 108. The processing element 18 may be any suitable electronic or other device configurable to perform the functions described herein. The defect may in the form of porosities, voids, unfused powders, dimensional variations, non-homogenous powders, improper microstructure, and/or cracks. If the indication of a defect is discovered, the processing element 18 may communicate an alert so that further action (e.g., further testing) may be taken, as shown in step 108.

In one implementation, the processing element 18 may be configured to compare a phase of the determined relationship to a reference to identify the indication of the defect, as shown in step 106A.

In another implementation, the processing element 18 may be configured to compare a magnitude of the determined relationship to a reference to identify the indication of a defect, as shown in step 106B. The processing element 18 may be further configured to identify the indication of the defect in an internal damping characteristic of the part 12.

In yet another implementation, the processing element 18 may be configured to compare the coherence function between the output and the input to a reference to identify the indication of a defect, as shown in step 106C, compare the determined modal parameters to a reference, as shown in 106D, or compare the characteristic time delays to a reference, as shown in step 106E.

The pre-established reference may be established by intentionally manufacturing a defective part with a known defect using the additive manufacturing process, examining the determined relationships to identify the indication of the known defect, and basing the pre-established reference and detection threshold on the identified indication. Additionally or alternatively, the pre-established references may also be based on models and simulations of a reference part.

The system 10 and method 100 may be used to inspect one part at a time or to simultaneously inspect a plurality of parts located on the build platform. The system 10 and method 100 may be used as or as a step in an initial or intermediate screening process to identify problems in the additive manufacturing process, and if a problem is found, the parts may then be subjected to a more extensive inspection. The system 10 and method 100 may be used to test a part before it is removed from the build platform. For example, the build platform itself may be installed in a test apparatus that implements the present invention. Following testing, the part may be removed from the build platform.

Applications of embodiments of the present invention may include inspecting metal parts produced using additive manufacturing processes in, e.g., the Nuclear Security Enterprise and/or the defence and aerospace industry. Additional applications include inspecting other high precision/high quality components, including those produced using conventional machining techniques, including non-metallic parts. Some such parts may be supported during impact to minimize the amount of damping imparted to the system.

Embodiments of the present invention may be adopted into one or more commonly accepted test standards, such as ASTM WK47031, New Guide for Nondestructive Testing of Additive Manufactured Metal Parts Used in Aerospace Applications; F2971-13, Standard Practice for Reporting Data for Test Specimens Prepared by Additive Manufacturing; F3122-14 Standard Guide for Evaluating Mechanical Properties of Metal Materials Made via Additive Manufacturing Processes; and ISO I ASTM52921-13, Standard Terminology for Additive Manufacturing-Coordinate Systems and Test Methodologies.

The present invention provides several advantages over prior art processes. Unlike prior art processes, the present invention may not simply evaluate the amplitude of the measured dynamic response, but rather it may evaluate the relationships between the output responses and the input excitation. The phase of the determined relationships is sensitive to the damping in the system, the coherence function is sensitive to non-linearity in the system, and the cross-correlation function is sensitive to reflections and unequal signal paths in the system. None of these measures are available to a system which analyses the output response without considering the input excitation. Failure modes anticipated in additively manufactured parts are expected to affect internal damping, non-linearity and reflections. In addition, the present invention may minimize or limit the amount of external damping imparted to the part being tested, including minimizing various forms of friction that might otherwise dissipate energy. This may be accomplished, for example, by supporting the build platform on air bearings, and/or using a non-contact transducer as the output mechanism. Using a measure sensitive to system damping and controlling external damping facilitates discriminating between good parts and bad parts based on system damping.

Unlike prior art processes, the present invention may directly measure the mechanical response of the part, not the radiated acoustic field, so that modes with low radiation efficiency will still be detected, and the measurements can be performed in a production environment in the presence of high levels of background noise.

Unlike prior art processes, the present invention may not use ultrasonic transducers. Ultrasonic transducers inherently have very little displacement capability and subsequently have very little power at low frequency. Ultrasonic transducers are only able to excite high frequency modes in parts and are not able to excite or detect low frequency modes, even though low frequency modes are likely to be most affected by the types of defects typically found in additively manufactured parts. Furthermore, exciting and/or measuring parts through contact with ultrasonic transducers, which generally require acoustic coupling, adds to system damping.

Unlike prior art processes, the present invention may not input energy directly into the parts being tested. Because prior art processes input energy directly into the parts, those processes must be adjusted for the size and shape of each part being tested. The present invention may input energy directly into the standard build plate used in additive manufacturing, which means that any part produced on a particular additive manufacturing machine can be tested without requiring any adjustments to excite the plate.

Although the invention has been described with reference to the one or more embodiments illustrated in the figures, it is understood that equivalents may be employed and substitutions made herein without departing from the scope of the invention as recited in the claims.

Having thus described one or more embodiments of the invention, what is claimed as new and desired to be protected by Letters Patent includes the following:

1. A system for the non-destructive, in-situ testing of one or more parts manufactured using an additive manufacturing process, the system comprising:
    an additive manufacturing build platform positioned in an additive manufacturing machine and configured to support the one or more parts during the additive manufacturing process;
    an input mechanism configured to excite with an excitation force the additive manufacturing build platform on which one or more parts are located to induce a dynamic response in the one or more parts;
    an output mechanism configured to sense the induced dynamic response in the one or more parts; and
    a processing element configured to determine a relationship between the excitation force and the dynamic response and to compare a phase of the determined relationship to a reference in order to identify an indication of a defect in the one or more parts, and to communicate an alert if the indication of the defect is identified.

2. The system as set forth in claim 1, wherein a plurality of parts located on the additive manufacturing build platform are tested simultaneously.

3. The system as set forth in claim 1, wherein the defect in the one or more parts is selected from the group consisting of: porosities, voids, unfused powders, dimensional variations, non-homogenous powders, improper microstructure, or cracks.

4. The system as set forth in claim 1, wherein the excitation force is selected from the group consisting of: impulsive vibrations, swept sinusoid vibrations, or random input vibrations.

5. The system as set forth in claim 1, wherein the excitation force excites the additive manufacturing build platform by introducing the excitation force directly to the additive manufacturing build platform so as to introduce the excitation force indirectly to the one or more parts located on the additive manufacturing build platform.

6. The system as set forth in claim 1, wherein the system is further configured to minimize external damping imparted to the one or more parts, including minimizing one or more forms of friction.

7. The system as set forth in claim 1, wherein the relationship between the excitation force and the dynamic response may include one or more selected from the group consisting of: a frequency response function, a coherence function, a cross-correlation function, or a cross-power spectrum.

8. The system as set forth in claim 1, wherein the processing element is configured to compare a magnitude of the determined relationship to a reference to identify the indication of the defect.

9. The system as set forth in claim 1, wherein the processing element is configured to compare a coherence function between the excitation force and the dynamic response to a reference to identify the indication of the defect.

10. The system as set forth in claim 1, wherein the processing element is configured to determine one or more modal parameters, and compare the one or modal parameters to a reference to identify the indication of the defect.

11. The system as set forth in claim 1, wherein the processing element is configured to determine a characteristic time delay, and compare the characteristic time delay to a reference to identify the indication of the defect.

12. A method for the non-destructive, in-situ testing of one or more parts manufactured using an additive manufacturing process, the method comprising:
    manufacturing a part with a known defect on an additive manufacturing build platform using additive manufacturing;
    exciting with an input mechanism the additive manufacturing build platform on which the part with the known defect is located by using an excitation force to induce a first dynamic response in the part with the known defect, the additive manufacturing build platform being positioned in an additive manufacturing machine and configured to support the part with the known defect during the additive manufacturing process;
    sensing with an output mechanism the first dynamic response in the part with the known defect;
    determining with an electronic processing element a relationship between the excitation force and the first dynamic response to identify an indication of the known defect;
    exciting with the input mechanism the additive manufacturing build platform used in additive manufacturing on which the one or more parts are located by using the excitation force to induce a second dynamic response in the one or more parts, the additive manufacturing build platform being positioned in the additive manufacturing machine and configured to support the one or more parts during the additive manufacturing process;
    sensing with the output mechanism the second dynamic response in the one or more parts; and
    determining with the electronic processing element a relationship between the excitation force and the second dynamic response to determine if the indication of the known defect is present in the relationship between the excitation force and the second dynamic response, and electronically communicating an alert if the indication of the known defect is identified.

13. The method as set forth in claim 12, wherein a plurality of parts located on the additive manufacturing build platform are tested simultaneously.

14. The method as set forth in claim 12, wherein the defect in the one or more parts is selected from the group consisting of: porosities, voids, unfused powders, dimensional variations, non-homogenous powders, improper microstructure, or cracks.

15. The method as set forth in claim 12, wherein the excitation force is selected from the group consisting of: impulsive vibrations, swept sinusoid vibrations, or random input vibrations.

16. The method as set forth in claim 12, wherein the excitation force excites the additive manufacturing build platform by introducing the excitation force directly to the additive manufacturing build platform so as to introduce the excitation force indirectly to the one or more parts located on the additive manufacturing build platform.

17. The method as set forth in claim 12, further including the step of minimizing external damping imparted to the one or more parts, including minimizing one or more forms of friction.

18. The method as set forth in claim 12, wherein the relationship between the excitation force and the dynamic response may include one or more selected from the group consisting of: a frequency response function, a coherence function, a cross-correlation function, or a cross-power spectrum.

19. The method as set forth in claim 12, wherein the processing element is configured to compare a phase of the determined relationship to a reference to identify the indication of the defect.

20. The method as set forth in claim 12, wherein the processing element is configured to compare a magnitude of the determined relationship to a reference to identify the indication of the defect.

21. The method as set forth in claim 12, wherein the processing element is configured to compare a coherence function between the excitation force and the dynamic response to a reference to identify the indication of the defect.

22. The method as set forth in claim 12, wherein the processing element is configured to determine one or more modal parameters, and compare the one or modal parameters to a reference to identify the indication of the defect.

23. The method as set forth in claim 12, wherein the processing element is configured to determine a characteristic time delay, and compare the characteristic time delay to a reference to identify the indication of the defect.

* * * * *